US008071117B2

(12) United States Patent
Cross et al.

(10) Patent No.: US 8,071,117 B2
(45) Date of Patent: Dec. 6, 2011

(54) PHEROMONES

(75) Inventors: Jeremy Vincent Cross, Kent (GB); David Robert Hall, Kent (GB)

(73) Assignees: East Malling Research Limited, Kent (GB); University of Greenwich, London (GB)

( * ) Notice: Subject to any disclaimer, the term of this patent is extended or adjusted under 35 U.S.C. 154(b) by 775 days.

(21) Appl. No.: 11/630,597

(22) PCT Filed: Jun. 27, 2005

(86) PCT No.: PCT/GB2005/002504
§ 371 (c)(1),
(2), (4) Date: Jun. 9, 2008

(87) PCT Pub. No.: WO2006/000798
PCT Pub. Date: Jan. 5, 2006

(65) Prior Publication Data
US 2008/0279810 A1 Nov. 13, 2008

(30) Foreign Application Priority Data

Jun. 25, 2004 (GB) .................................. 0414359.0
Oct. 20, 2004 (GB) .................................. 0423294.8

(51) Int. Cl.
*A01N 25/34* (2006.01)
(52) U.S. Cl. .............. 424/409; 43/107; 43/131; 424/84; 424/405; 424/406; 424/411; 514/529; 514/546
(58) Field of Classification Search .................. 514/529, 514/546
See application file for complete search history.

(56) References Cited

FOREIGN PATENT DOCUMENTS

EP 0130951 B1 4/1991
EP 0367598 B1 9/1993

OTHER PUBLICATIONS

Ishmuratov, et al., "A New Approach to the Synthesis of Racemic Analogs of 1,5-Dimethyl-Branched Insect Pheromones from 4-Methyltetrahydropyran" *Russian Chemical Bulletin* 52(3):740-744 (2003).
Odinokov, et al., "Insect Pheromones and Their Analogs. XLVI. Synthesis of 13RS-Hydroxy-5Z-Tetradecenoic Acid, the Acyclic Precursor of the Macrolide Component of Cryptolestes Pusillus Pheromone" Khimiya Prirodnykh Soedinenii, 1:150-155 (1993).
Sinha, et al., "A General Approach to Enantiomerically Pure Methylcarbinols. Asymmetric Synthesis of Antibiotic (−)-A26771B and the WCR Sex Pheromone" *J. Org. Chem.* 58:7789-7796 (1993).
Baudouy, et al., "Stereoselective Synthesis of the Pheromone, (3S, 5E)-(−)-3,9-Dimethyl-6-Isopropyldeca-5,8-Dien-1-yl Acetate from Aonidiella Citrina" *Tetrahedron* 47(48) 10015-10022 (1991).
Dasaradhi, et al., "A New Approach for Synthesis of Pheromones: S-Hexadecanolide and 2-Methylheptadecanet†" *Indian Journal of Chemistry* 30B:417-418 (1991).

(Continued)

*Primary Examiner* — Neil Levy
(74) *Attorney, Agent, or Firm* — Foley & Lardner LLP; Stephen E. Reiter

(57) ABSTRACT

The apple leaf midge and raspberry cane midge pheromones have been found to be acetoxyheptadecenone and acetoxyundecanone, respectively, and uses for these and related compounds are provided, including monitoring population levels of the midge and control of midge populations by disrupting mating patterns.

32 Claims, 4 Drawing Sheets

OTHER PUBLICATIONS

Figure 1:
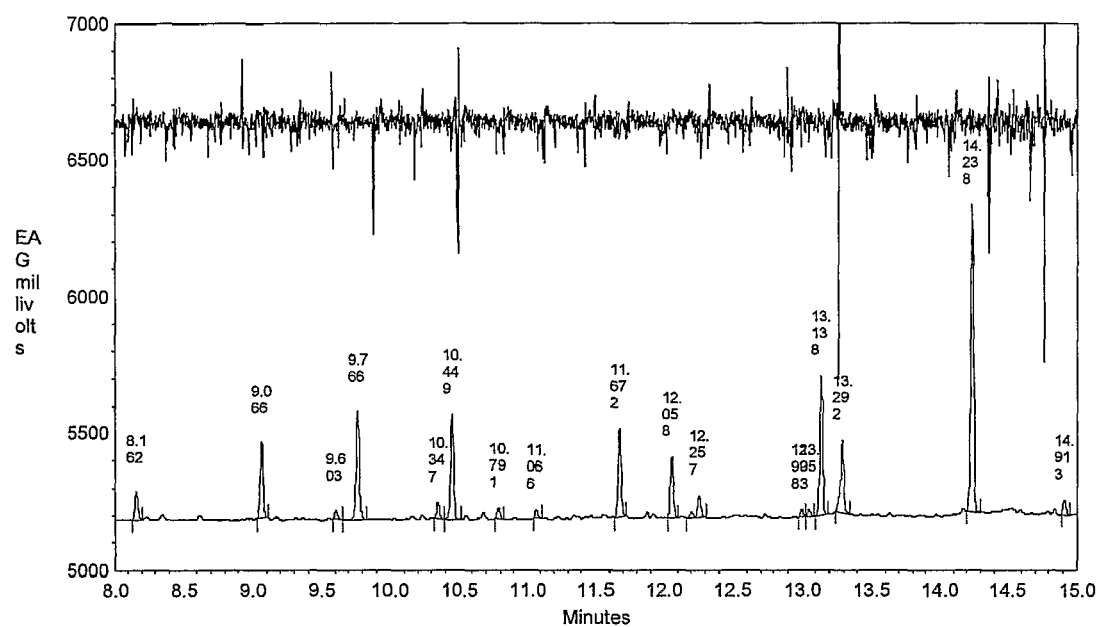

Odinokov, et al., "Ozonolysis of Alkenes and Study of the Reactions of Polyfunctional Compounds. XXX. Synthesis of Acetates of Diastereomeric (.—.)-3,7-Dimethylpentadecan-2-01 and Its 7-Nor Analog—Sex Pheromones of Pine Sawflies of the Genera Diprion and Neodiprion" *Zhurnal Organicheskoi Khimii* 22(5):953-957 (1986).

Caine et al., "A new synthesis of the California Red Scale Pheromone from S-(+)-carvone." Tetradehron Letters 25(47):5359-5362 (1984).

Cooke, et al., "Charge-Directed Conjugate Addition Reactions in the Preparation of Substituted Methyl Ketones" *J. Org. Chem.* 47:4955-4963 (1982).

Tolstikov, et al., "Pheromones of Insects and Their Analogs V. New Approach to the Synthesis of Sex Pheromones of Insects of the Order Lepidoptera Based on the Selective Ozonolysis of 1-Methyl-1Z, 5Z-Cyclooctadiene" *Khimiya Prirodnykh Soedinenii* 239-245 (1982).

Mori, et al., "Determination of the Absolute Configuration at C-6 and C-7 of Serricomin (4, 6-Dimethyl-7-Hydroxy-3-Nonanone), the Sex Pheromone of the Cigarette Beetle" *Tetrahedron Letters* 22:1127-1130 (1981).

Magnusson, G., "Preparation of Pine Sawfly (*Hymenoptera: Diprionidae*) Sex Attractants and Analogues with Possible Biological Activity" *Tetrahedron* 34:1385-1388 (1978).

Garbers, et al., "Terpenoid Synthesis V. Electrophilic Addition Reactions in the Synthesis of the Ocimenones, the Rose Oxides, and a Pheromone of *IPS Paraconfusus*" *Tetrahedron Letters* 19:1625-1628 (1976).

Takacs and Vayalakkada, "Product subclass 4: Palladium-Alkene complexes." Science of Synthesis, 1:319-387, 2002.

Tsuji, et al., "Regioselective Oxidation of Internal Olefins Bearing Neighboring Oxygen Functions by Means of Palladium Catalysts. Preparation of β-Alkoxy or Acetoxy Ketones from Allyl and Homoallyl Ethers or Esters" *Tetrahedron Letters* 23(26):2679-2682 (1982).

Subraminiam, et al., "Simple Synthesis of Prostanoid Synthons" *Tetrahedron Letters* 5:495-496 (1978).

Friour, et al., "Organomanganese(II) Reagents; $X^1$. A Convenient Preparation of Various Acetoxyketones, Keto-Nitriles, Keto-Esters, Keto-Acids, Diketones, and Heterocyclic Ketones (Acylheterocycles) Via Acylation of Organomanganese(II) Reagents" *Synthesis* pp. 50-54 (1985).

Ochiai, et al., "Conjugate Addition of Acyloxy Groups to Alkynylphenyliodonium Tetrafluoroborates under Both Basic and Acidic Conditions. Synthesis of α-Acyloxy Ketones" *J. Org. Chem.* 54:4038-4041 (1989).

Midgley, et al., "Selectivity of Radical Formation in the Reaction of Carbonyl Compounds with Manganese(III) Acetate" *J. Chem. Soc. Perkin Trans.* pp. 1103-1108 (1987).

Molander, et al., "Intramolecular Nucleophilic Acyl Substitution Reactions Mediated by Samarium(II) Idodide: A Convergent Approach to the Preparation of Enantiomerically Enriched 4-Hudroxy Ketones from 3-lodopropyl Carboxylates" *J. Org. Chem.* 59:3445-3452 (1994).

Sakaguchi, et al., "Oxidation of Allenes and Alkynes with Hydrogen Peroxide Catalyzed by Cetylpyridinium Peroxotungstophosphate (PCWP)" *J. Org. Chem.* 59:5681-5686 (1994).

Dang, et al., "Homolytic Aldol Reactions: Thiol-Catalysed Radical-Chain Addition of Aldehydes to Enol Esters and to Silyl Enol Ethers" *Chem. Commun.* pp. 2201-2202 (1996).

Fischli, A., "108. Electrofungal Fragmentation of Alkylcobalamin Derivatives Using Cob(I)alamin and Heptamethyl Cob(I)yrinate as Catalysts)" *Helvetica Chimica Acta* 65(4):1167-1190 (1982).

Kirchanov, et al., "Synthesis of Higher 1,3-diols from Ethylene and Carboxylic Acid Chlorides" *Izvestiya Akademii Nauk SSSR, Seriya Khimicheskaya* 4:909-911 (1981).

Moroe, et al., "Dihydrojasmone from Enanthal" JP 450 247 71B B4 (*Takasago Perfumery Co., Ltd.,*), Aug. 18, 1970.

Reed, et al., "The Mercury (II) Catalyzed, One-Pot Oxidation of Terminal Alkynes by Sodium Perborate in Acetic Acid" *Synthetic Communications* 19(13 & 14):2595-2602 (1989).

Fuji, et al., "2,2-Dimethyl-1-1,3-Oxathiane 3,3-Dioxide: A γ-Hydroxypropyl Anion Equivalent" *Synthesis* pp. 852-858 (1991).

Matsumoto, et al., "Preparation of Ketones as Intermediates for Drugs, Agrochemicals and Perfumes" JP 63 063632 A2 (*Sagami Chemical Research Center, Japan, Nippon Mining Co.*) Mar. 22, 1988.

Diallo, et al., "Triacylbenzenes and Long-Chain Volatile Ketones from *Cochlospermum Tinctorium* Rhizome" *Phytochemistry* 30(12):4153-4156 (1991).

Schlichting, et al., "The Gamma—Lactone of 3-Tridecyl-4-Hydroxy-2-Butenoic Acid" *Journal of American Chemical Society* 74:5547 (1952).

Negishi, et al., "A General Multi-Carbon Homologation of Olefins via Hydroboration-Carbonylation" *Synthesis* 4:196-197 (1972).

Kashman, et al., "New Compounds from Avocado Pear" *Tetrahedron* 25:4617-4631 (1969).

Sunko, et al., "Studies in the Sphingolipids Series. II. Synthesis of Enantiomeric Sphingines" *Institute of Physiology and Chemistry Medical Faculty, Univ. Of Zagreb* pp. 1523-1528 (1953).

Kobayashi, et al., "Synthesis of (±)-Dendrotrifidiol and Its Naturally Occurring Analogs" *Agric. Biol. Chem.* 41(4):691-695 (1977).

Chauhan, et al., "Nonadecan-7-OL-2-One, an Aliphatic Ketol from *Diospyros Peregrina*" *Phystochemistry* 19:2637-2638 (1980).

International Seach report from PCT Application PCT/GB2005/002504.

PHEROMONES

The present invention relates to novel compounds attractive to certain insect species, uses therefor, and compositions thereof.

Pheromones were first recognised over a hundred years ago, when it was noted that male moths would fly against the wind direction in order to reach a sexually attractive female. However, it was not until the late 1950's that the first chemical structure for an insect pheromone was established.

Sex pheromones are volatile substances, produced by individuals of one sex of a species (usually the female), and which attract the opposite sex for the purposes of mating. They are generally produced in small, sometimes very small, quantities, and can be very difficult to identify. Those pheromones that have successfully been identified take a number of different forms, and are frequently long chain, saturated or unsaturated alcohols, esters or aldehydes, though pheromones with many other chemical structures have been identified, and are often blends of two or more compounds.

By their nature, pheromones are often powerful attractants, and an artificial source of a pheromone can severely disrupt the natural mate location process of the originating insect species. Thus, it is potentially useful to be able to isolate and characterise pheromones from pest or beneficial species.

As noted above, levels of natural pheromone production are sometimes exceedingly low and, in addition, natural production is also generally limited to a specific phase in the life cycle. Levels of production of pheromones vary greatly but are typically measurable in nanogram (1,000th of 1,000,000th of a gram) range, so that they can be very difficult to detect and characterise.

The apple leaf midge (*Dasineura mali* (Kieffer)) has been demonstrated to rely on pheromones for mating. The pheromone is believed to be produced by a small gland which is visible, with the aid of a microscope, at the base of the female midge's ovipositor. This midge is a particularly important pest in apple orchards in many apple producing areas of the world, and various attempts have been made to isolate and characterise the pheromone.

Previous work has shown that male apple leaf midges are attracted to virgin females in both laboratory and field bioassays. Researchers in New Zealand spent over five years trying to identify the apple leaf midge pheromone by extracting ovipositors, but never obtained enough material for elucidation of the structure (Harris, M. O., Foster, S. P., Agee, K., and Dhana, S. (1996), Sex pheromone communication in the apple leaf-curling midge (*Dasineura mali*), *Proceedings of New Zealand Plant Protection Conference*, 49: 52-58).

Attraction of male apple leaf midges by females was demonstrated in a laboratory bioassay, but it was not possible to isolate and identify the pheromone (Heath, J. J., Gaul, S. O., Nash, D. M. and Smith, R. F. (1998), Evidence for a female-produced sex pheromone in the apple leaf midge, *Dasineura mali* (Kieffer) (Diptera: Cecidomyiidae), *Canadian Entomologist* 130: 109-110).

Wendell Roelofs (Cornell University, USA) reported obtaining an EAG response from a male apple leaf midge in linked GC-EAG analyses of pheromone collected on an SPME fibre, reported at a meeting in 1998.

The raspberry cane midge, *Resseliella theobaldi* (Barnes), is an important pest of raspberry, both in the UK, and in many other areas of the world. The adult midge lays eggs in splits in young canes, and larvae feed on the pith beneath the rind, causing penetrating lesions which allow entry of diseases, such as the cane blight fungus *Leptosphaeria coniothyriunm*. There are three or more generations per annum.

The pest is controlled, currently, by routine sprays of an organophosphorus insecticide, chlorpyrifos, or similar broad spectrum insecticidal compound, applied to control the first generation in spring. This also prevents significant damage by the subsequent generations, although population increase occurs. Traditionally, a spray was applied as a matter of routine, in late April or early May, when the spawn was 20-30 cm high, and again about two weeks later. However, more recently, a temperature-based forecasting model has been developed by the Scottish Crops Research Institute for predicting spring oviposition, in the UK, by the raspberry cane midge, to aid better timing of sprays. Spray warnings are made available to growers. First oviposition occurs when a temperature sum of 339° C. days above 4° C. is accumulated. Values are interpolated from the nearest meteorological station, making a correction for the altitude and aspect of the particular location. The forecast is considered to be accurate to ±5 days. The problem with this system is that it results in routine use of insecticides in raspberry plantations and it does nothing to diminish the use of organophosphate insecticides in this crop.

The use of organophosphate insecticides, such as chlorpyrifos, is undesirable, since they are toxic to humans and wildlife as well as being harmful to beneficial arthropods, and residues of the insecticide often remain in fruit supplied to the consumer. For example, organophosphate residues were found in 22% of samples of UK produced raspberry fruit (KG Fruits Residues Data).

The existence of a female sex pheromone in the raspberry cane midge had not previously been proven, but it was known that it was likely that one existed, by analogy with related species. An isolated pheromone would be useful for monitoring the pest, thereby making the forecasting model redundant, and obviating the need for routine sprays, spraying only being necessary if the pest were detected, or possibly not at all, where the pheromone was associated with a trap to lure and kill the pest, for example. It could also be used for population control by mating disruption, lure and kill, or by mass trapping approaches.

Thus, no technique has, so far, been successful in isolating the apple leaf midge or raspberry cane midge pheromones, for example, and the isolation of these and related substances remains an important aim in the agriculture industry.

Surprisingly, we have now been able to identify a novel range of compounds to which the apple leaf midge and raspberry cane midge pheromones belong.

Thus, in a first aspect, there is provided a composition of matter comprising a pheromone substance and a carrier therefor, the pheromone substance being a $C_{9-19}$ oxoalkyl or oxoalkenyl molecule substituted with a lower alkanoyloxy group.

The carrier or vehicle may be any suitable substance or medium, ranging from a simple solvent, generally liquid or solid, such as ethanol or wax, through to substrates such as wicking materials. Solvents need only sparingly dissolve the pheromone substance, as the such substances generally need only be used in very small amounts. The solvent may be selected based on its other physical characteristics, such as vapour pressure such that, on exposure to air, the solvent may readily evaporate to release the pheromone substance.

The carrier may enable the pheromone substance to be retained in the form of a reservoir for dispensing into a device employing the pheromone, or may act to transport the pheromone and to facilitate handling, for example. Wicks may be sealed prior to use to prevent release of pheromone other than at the desired site.

The pheromone substance is preferably identical to the natural substance for the target animal, and is generally referred to simply as a "pheromone" herein, although it will be understood that analogues and enantiomers of the naturally active substance may be used and which possess pheromone activity, and are included in the definition of pheromone substances. Likewise, where a racemic mixture of substances has pheromone activity, even where only one enantiomer is active, then such mixtures are also included in the term.

Preferred molecules have between 11 and 17 carbons, inclusive, in the alkyl or akenyl chain.

For the avoidance of doubt, aldehyde groups are not included in the term "oxo".

It is preferred that the lower alkanoyloxy group is linked to a methylene group, to form a group >CH—O(CO)Alk where —O(CO)Alk represents the alkanoyloxy group, and >CH— represents a saturated carbon linked to at least two other carbons, and preferably only two other carbons.

It is particularly preferred that the pheromone consist only of the oxoalkyl or oxoalkenyl backbone possessing only the alkanoyloxy and oxo substituents.

The compounds of the present invention are preferably straight chain compounds, and may be saturated or unsaturated.

Unsaturated compounds of the invention may be unsaturated at a plurality of positions, but preferably no more than three. It is preferred that compounds of the invention are alkanes, or are singly or doubly unsaturated alkenes. Alkanes and singly unsaturated compounds are most preferred. Where the compound is multiply unsaturated, it is preferred that the double bonds are not located on consecutive carbon atoms.

The double bond, or bonds, where present, may be located at any position, but it is preferred that they not be located at either terminus of the molecule. Thus, it is preferred to avoid the 1- and 16-positions in a $C_{17}$ molecule, for example. More preferably, any double bonds are preferably located 3 or more carbon atoms removed from the end of the molecule.

Preferred compounds of the present invention are heptadecene straight chain compounds, wherein the double bond is located at a position between carbon atoms 4 and 13, preferably at the 7, 8 or 9 position, and especially at the 8 position.

Other preferred compounds are the undecanes, especially the 2-alkanoyloxy, 5-oxo and the 2-oxo, 5-alkanoyloxy compounds, the 2-alkanoyloxy, 5-oxo being most preferred.

Tridecane, tridecene, pentadecane and pentadecene compounds are also preferred.

The oxo group may be located at any position on the molecule, provided that it forms a >C=O group, rather than a =C=O or —CHO group. Generally, no carbon in the backbone of the molecule will be involved in any more than one of: the ketone; a double bond; and, linkage with the alkanoyloxy group.

Preferably, the oxo group, also referred to herein as the ketone group when referred to jointly with the carbon of the backbone of the molecule to which it is attached, is located at the 2-position. Where the alkanoyloxy is situated at the 2-position, then the oxo may preferably be located at a position between 5- and 9-, preferably at the 5-position. In any event, the 5-position is a preferred position for the oxo moiety.

The lower alkanoyloxy group is preferably a $C_{1-6}$ alkanoyloxy, such as the butyryloxy, propionyloxy or acetoxy groups, and is especially preferably the acetoxy group.

Where the compound of the invention has only the one double bond, then it is generally preferred that the ketone group be located proximal to the double bond whilst the alkanoyloxy group is located distal to the double bond. In the case of the heptadecene molecule, for example, it is preferred that the ketone group is located at any of carbon atoms 2 to 7. It is particularly preferred that the ketone group be located at the 2 position.

Also, in this embodiment, the alkanoyloxy group may be located anywhere on the latter portion of the molecule, distal to the double bond, such as on any of the positions between 10 and 17, but is preferably located at position 13 of the heptadecene molecule, for example.

The length of the molecule is not critical to the present invention. However, molecules having lengths of 9, 11, 13, 15, 17 and 19 carbons are preferred, as it has been established that biologically active compounds of this nature tend to progress in homologous series increasing by two carbons. In addition, based on a most preferred compound, 13-acetoxy-8-heptadecen-2-one, then it is preferred that, where there is at least one double bond, an increase or decrease of 2 carbons be effected at one or other side of the double bond.

Thus, a preferred 15 carbon compound is 11-acetoxy-6-pentadecen-2-one, while another is 13-acetoxy-6-pentadecen-2-one, and another is 13-acetoxy-8-pentadecen-2-one. Preferred saturated compounds include: 11-acetoxypentadecan-2-one, 13-acetoxypentadecan-2-one, and 13-acetoxypentadecan-2-one. Preferred dienes include: 11-acetoxypentadec-6,8-dien-2-one, 13-acetoxypentadec-4,6-diene-2-one, and 13-acetoxypentadec-8,10-diene-2-one.

Preferred 11 carbon compounds include 8-acetoxy-6-undecen-2-one, 2-acetoxy-6-undecen-5-one, 8-acetoxy-4-undecen-2-one, 6-acetoxy-6-undecen-2-one, 2-acetoxy-6-undecen-8-one, 2-acetoxy-4-undecen-8-one, and 2-acetoxy-8-undecen-6-one.

Preferred saturated compounds include: 6-acetoxyundecan-2-one, 8-acetoxyundecan-2-one, 4-acetoxyundecan-2-one, 2-acetoxyundecan-6-one, 2-acetoxyundecan-8-one, 2-acetoxyundecan-5-one and 2-acetoxyundecan-4-one. Preferred dienes include 8-acetoxypentadec-4,6-dien-2-one and 2-acetoxypentadec-4,6-dien-8-one.

Preferred 19 carbon compounds include 13-acetoxy-8-nonadecen-2-one, 15-acetoxy-8-nonadecen-2-one, 15-acetoxy-10-nonadecen-2-one, 13-acetoxy-10-nonadecen-2-one, and 15-acetoxy-6-nonadecen-2-one. Preferred 19 carbon dienes include: 13-acetoxynonadec-6,8-diene-2-one, 15-acetoxynonadec-11,13-diene-2-one, 15-acetoxynonadec-6,10-diene-2-one, 13-acetoxynonadec-8,10-diene-2-one, and 15-acetoxynonadec-4,6-diene-2-one.

Preferred 17 carbon compounds include 13-acetoxy-8-heptadecen-2-one, 15-acetoxy-8-heptadecen-2-one, 15-acetoxy-10-heptadecen-2-one, 13-acetoxy-10-heptadecen-2-one, 15-acetoxy-6-heptadecen-2-one, 2-acetoxy-8-heptadecen-13-one, 2-acetoxy-8-heptadecen-15-one, 2-acetoxy-10-heptadecen-15-one, 2-acetoxy-10-heptadecen-13-one, and 2-acetoxy-6-heptadecen-15-one. Preferred 17 carbon dienes include: 13-acetoxyheptadec-6,8-diene-2-one, 15-acetoxyheptadec-11,13-diene-2-one, 15-acetoxyheptadec-6,10-diene-2-one, 13-acetoxyheptadec-8,10-diene-2-one, and 15-acetoxyheptadec-4,6-diene-2-one.

The corresponding 8, 10, 12, 14, 16 and 18 carbon compounds to those listed above are also preferred, especially when they contain no carbon-carbon double bond in the backbone.

It will be appreciated that the alkanoyloxy group may be in either of the R and S configurations. However, the configuration of the acetoxy group is not generally important to the present invention, as racemic mixtures of the compounds of the invention have proven to be highly effective. For example, in one test, in one day, a racemic mixture of (Z)-13-acetoxy-8-heptadecen-2-one, when released at approximately 1 ng/hr, attracted 1,600 apple leaf midges to a trap. Similar field tests using racemic 2-acetoxy-5-undecanone attracted a significant number of raspberry cane midges to a trap.

Where racemic mixtures are used, or useful, it is convenient to employ the ratio of enantiomers that occur as a result of the synthetic procedure, in order to avoid unnecessary process steps. Provided that the mixtures are effective to attract the target animal, then it does not matter what the ratio is, and even trace amounts of the active enantiomer in the mixture, if one enantiomer is more active than the other, will still have the desired effect, provided that the less active or inactive enantiomer does not serve to block, disable or otherwise mask the effect of the active enantiomer in the chosen circumstances. Testing for such a conflict is straightforward and, while the preparation of industrial quantities of a pure enantiomer is not generally commercially attractive, the isolation of small quantities for field testing of pheromones is readily achieved by those skilled in the art, such as by chiral gas chromatography or HPLC, for example. If a racemic mixture fails to attract the target animal, but a pure enantiomer succeeds, then it is apparent that one enantiomer is masking the effect of the other. So far, we have not observed any such masking effect in the compounds of the invention.

It has generally been found to be the case that one enantiomer is biologically active, while the other is not. Activity is considered in relative terms, here, but is often absolute. Moreover, in some species, while the enantiomer produced by the insect is attractive, the other enantiomer has an inhibitory effect on attractiveness. In such a cases, it will be appreciated that it is desirable to minimise the amount of the inhibitory enantiomer, and preferably to exclude it altogether. This may advantageously be achieved by the use of selective synthesis, for example, such as is illustrated below.

Where an acetoxy group is referred to herein, this includes reference to any alkanoyloxy group, unless otherwise apparent or indicated. In general, the acetoxy group is the preferred alkanoyloxy group.

It will be appreciated that, where the compound possesses one or more double bonds, then the compound may be in either the Z or E configurations in relation to each double bond. Where there is a single double bond, then the Z configuration is especially preferred.

A preferred compound of the present invention is an acetoxyheptadecenone.

Another preferred compound is an acetoxyundecanone.

The structure established for both the apple leaf midge pheromone and the raspberry cane midge share certain biogenetic relationships to pheromones of other midges, but are sufficiently different that they would not have been discovered by random screening of other midge pheromones, or related compounds.

Thus, particularly preferred compounds of the invention have the following formula:

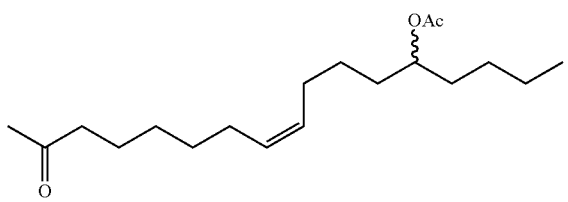

and are referred to as (Z)-13-acetoxy-8-heptadecen-2-one.

The compound produced by female apple leaf midges has been characterised as being this compound.

Likewise, another particularly preferred compound of the invention has the formula:

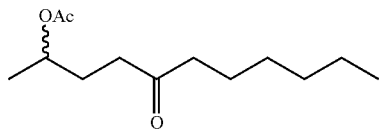

and is referred to as 2-acetoxy-5-undecanone. The compound produced by female raspberry cane midges has been characterised as being this compound.

A further preferred compound of the invention has the formula:

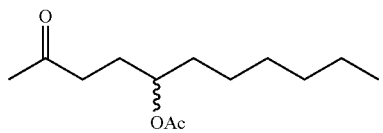

and is referred to as 5-acetoxy-2-undecanone.

In an alternative aspect, the present invention provides a molecule as defined above. In particular, the present invention provides a $C_{9-19}$ oxoalkyl or oxoalkenyl molecule substituted with a lower alkanoyloxy group, and wherein the alkanoyloxy group is attached to a methylene constituent of the oxoalkyl or oxoalkenyl molecule.

One group of particularly preferred compounds of the invention has the formula (Z)-13-acetoxy-8-heptadecen-2-one. While we have established that only one of the R and S isomers is significantly attractive to male apple leaf midges, we have also established that racemic mixtures work exceptionally well, so that there is no need to use enantiomerically pure material.

A further preferred compound of the invention is 2-acetoxy-5-undecanone. While it is highly likely that one or other of the R and S isomers is more attractive to raspberry cane midges than the other, racemic mixtures have been demonstrated to work exceptionally well, so that there is no need to use enantiomerically pure material. Nevertheless, the S compound appears to be the naturally occurring compound, and is the preferred compound of this aspect of the invention.

The preferred compounds of the present invention have been shown to be identical to the naturally occurring pheromones by mass spectrometry, for example, and 13-acetoxy-8-heptadecen-2-one has been demonstrated to have a strongly attractive effect on the male apple leaf midge, for example. Other compounds of the invention are expected to have similar effects on other insects, especially closely related species, particularly other midges, and limited field trials with other compounds of the invention have attracted other, as yet unidentified, midges, thereby establishing that many midges share this pheromone structure.

In the case of the raspberry cane midge, three other saturated C11 chain compounds, each occurring at about 30% of the concentration of 2-acetoxy-5-undecanone, are also detected in volatiles from the female raspberry cane midge, but not from the male raspberry cane midges, and are: 2-undecanol; 2-undecanone; and, 2-acetoxy undecane, each existing as optical isomers, other than 2-undecanone. Three corresponding C9 chain compounds (2-nonanol, 2-nonanone, and 2-acetoxy nonane) are also detected, but in considerably smaller quantities, each occurring at about 3% of the level of 2-acetoxy-5-undecanone, and appear not to be essential to the synthetic route.

Use of any of these compounds in the methods of the invention is provided, and especially where one or more of them is used in combination with compounds of the invention. In general, the use of analogues of these compounds having the same carbon length backbone as a preferred compound with which they are used in combination to disrupt the mating patterns of target insects is a preferred feature of the present invention.

The pheromones of the present invention may be made by any suitable means, although isolation from the natural source is not feasible in the absence of genetic modification. Even if the female apple leaf midge were genetically modified to produce large quantities of the pheromone, it is unlikely that commercially useful quantities could be isolated.

While it is generally feasible to modify organisms to produce precursors, or even the final product of the present invention, it is generally preferred simply to employ straightforward chemical synthesis, such as is illustrated hereinbelow.

Owing to the extreme potency of the compounds of the present invention, it is not necessary that the process for the preparation of the compounds be particularly efficient, as amounts of less than 1 μg may be used in effective dispensers or traps, for example, for the apple leaf midge. The raspberry cane midge produces considerably larger quantities of pheromone, but quantities of less than 1 mg are still, generally, sufficient. While amounts of very substantially less than 1 μg, such as in the order of a few pg, may be used and may be effective, it is not generally desired to reduce the amounts to this sort of level, simply owing to the difficulty of handling such small quantities. However, where it is desired simply to emulate a single female midge, for example, then traps, or other apparatus, using extremely small quantities of the compounds of the invention, may be employed.

It will be appreciated that pheromones are synthesised by many animals. Regarding the present invention, preferred target animals are insects and especially midges, particularly commercial crop and especially food crop midges, including those for grain (such as wheat), olive, raspberry, apple, blackcurrant, rhubarb, blackberry, plum, cherry, blueberry, the rosaceae and the cruciferae, particularly the brasica pod midge and swede midge, as well as other plant feeding midges that have agricultural, horticultural, ornamental or forestry crops or plants as their host plant.

The compounds of the present invention may be used as desired. In general, they are suitable to attract midges or to interfere with the natural mate location process, and the preferred compounds of the present invention attract the males of the apple leaf midge and the raspberry cane midge.

This attraction may be put to any appropriate or desired use. For example, a simple dispenser may be set up at a location remote from a target area, such as an orchard, but within detectable distance, thereby to attract male midges away from the orchard and prevent fertilisation of female midges in the orchard. While the males remain susceptible to the pheromone, then the artificial supply of the pheromone will act to ensure that, as far as possible, the midges remain away from the females in the orchard.

When used in this fashion, it is preferred that the pheromone be suitably formulated to release it at an appropriate rate into the atmosphere and to protect it from degradation through the effects of temperature, oxygen and/or sunlight, for example.

The apple leaf midge occurs in relatively well-defined generations in the UK and Europe, for example. Traps baited with the pheromone are suitable to provide a means of monitoring the pattern of emergence. As the traps are simple to use and specific for the target pest, they can be used by the growers themselves to optimise the timing of application of insecticide, so as to maximise the effect against the pest, and to minimise the effect on important beneficial insects, such as the parasitic wasp *Platygaster demades* or the predatory flower bugs *Anthocoris nemorum* and *Anthocoris nemoralis*. Similar considerations apply to the raspberry cane midge and, indeed, other insect pests.

For example, traps baited with pheromone may be used to verify the presence or absence of the pest in particular areas or places, such as in apple orchards in which the midge is believed not to occur, or in consignments of fruit for export or import, where fruit quarantine restrictions apply. In the case of the raspberry cane midge, determination of the presence or absence of the midge is important in determining whether any treatment is necessary. Countries where the target midge is officially absent may use suitably baited traps to confirm the absence of midges either in consignments or areas suspected of, or liable to, contamination, for example.

Given the extremely small quantities of compounds of the invention necessary to attract midges, then it is not generally important to the invention as to the nature of the substrate upon which the pheromone is carried, provided that the substrate permits dispersal of the pheromone into the atmosphere.

Suitable substrates include polyethylene, rubber, cotton wool, cellulose fibres, glass or ceramics, and these may take the form of supports or containers, for example.

The amount of pheromone employed will often be very small, and it will be appropriate to employ amounts that compete effectively with, or even overwhelm, any naturally occurring pheromone in the area. Nevertheless, if too great a quantity of pheromone is employed, this can overwhelm the insects' sensors. In certain circumstances, it may be appropriate to simply overwhelm the insect in such a fashion, such as in an orchard so as to render the females undetectable by the males, but it will be appreciated that the overwhelmed insect will not be able to detect the concentration gradient necessary to attract it to the source.

The synthetic pheromone may be dispensed from formulations such as microcapsules or twist-ties, such as are commonly used for disruption of the mating of moth pests.

In a particularly preferred embodiment, the present invention provides a trap loaded with at least one compound of the present invention. Insects attracted to the trap may be collected for counting, or investigation, for example, or a toxic substance may be incorporated into the trap to kill any insects caught.

Such traps may take any suitable form, and killing traps need not necessarily incorporate toxic substances, the insects being optionally killed by other means, such as drowning or electrocution. Even where the insects are not killed, the trap can serve to remove the male insects from the locale of the female insects, to prevent breeding.

Suitable forms of device for use in the present invention include traps that retain the insect until dead, such as sticky, water and oil traps, and devices that contaminate the insect with a killing agent, such as an insecticide, fungus or virus, that kills the insect later.

Traps may also be placed within an orchard to overwhelm the pheromones emitted by the females, so that the males simply cannot locate the females. In this respect, a trap need be nothing more than the simple apparatus alluded to above, being simply, for example, a protected wick able to dispense pheromone.

The wick or trap may be adapted to emit a pheromone for a period at least equivalent to the breeding season(s) of the midge, although highly aromatic pheromones may not lend themselves to such constructs. However, the midge may well have an extended breeding season, or repeated breeding season, in which case, in an alternative, the present invention provides a wick or trap capable of emitting pheromone for a period of time, especially about two weeks, and generally between about 1 and 4 weeks and up to 6 weeks, which may be rotated or replaced by subsequent similar traps.

The traps of the present invention may be provided in made-up form, where the compound of the invention has already been applied. In such an instance, depending on the half life of the compound, the compound may be exposed, or may be sealed in conventional manner, such as is standard with other aromatic dispensers, the seal only being removed once the trap is in place.

Alternatively, the traps may be sold separately, and the compound of the invention provided in dispensable format so that an amount may be applied to trap, once the trap is in place. Thus, the present invention may provide the compound in a sachet or other dispenser.

In a further embodiment of the present invention, a device may be used that contaminates the male insects with a powder containing the pheromone substance itself. The contaminated males then fly off and provide a source of mating disruption by permeating the atmosphere with the pheromone substance, or by attracting other males to the contaminated males, rather than to real females.

Given the potency of the compounds of the invention, while it is generally preferable to use the substantially pure form of the compound, the compound may also be provided in association with a vehicle. The vehicle may facilitate application of the compound to the desired location and may comprise, for example, a volatile vehicle, such as ethanol, which would not interfere with the compound, and which would evaporate quickly to leave the compound of the invention.

The present invention will now be illustrated further by the following, non-limiting Examples.

EXAMPLE 1

Identification of Natural Pheromone of Apple Leaf Midge (*Dasineura mali* (Kieffer))

During the months of August and September 2003, pheromone was collected from virgin female apple leaf midges, by passing charcoal-purified air over the midges in a glass container, and trapping volatiles on Porapak Q (SKC, Inc., USA). Volatiles were collected from 2191 female midges over this two month period. Volatiles were collected from 806 males in an identical manner.

Collections were analysed by gas chromatography (GC) linked to electroantennographic (EAG) recording from a male midge, using polar and non-polar GC columns. A single response was observed on both columns, and the retention times relative to those of saturated hydrocarbons and acetates were determined. Analysis of collections of volatiles from male midges did not elicit an EAG response from males or females.

Collections were analysed by GC coupled to mass spectrometry (MS) using similar polar and non-polar GC columns. In female collections, small peaks were observed at the retention times corresponding to those of the EAG responses on the two columns, and these had the same mass spectra in both electron impact (EI) and chemical ionisation, with isobutane, (CI) modes. This component was estimated to be produced at 1.5 pg/female/hr. It could not be detected in collections from male midges.

The EI and CI mass spectra were characteristic, but provided little information as to the structure, and it was uncertain as to what the molecular weight was. Comparison of GC retention times and mass spectra with those of all other midge pheromones, so far identified, indicated the apple leaf midge pheromone had a rather different structure, however. GC retention times and mass spectra were compared with those of a wide range of pheromones and related compounds.

A significant breakthrough was the finding that unsaturated heptadecen-2-ones had CI mass spectra with several similarities to that of the midge pheromone. Furthermore, catalytic hydrogenation of the pheromone gave a product indicating that the pheromone had a single double bond and confirming the presence of a methyl ketone moiety.

These data supported a structure of a 17-carbon methyl ketone with an acetoxy group and double bond. Synthesis of 16-acetoxy-heptadecan-2-one and determination of GC retention times and mass spectra supported this.

All isomers of acetoxy-heptadecane were synthesised, and GC retention times and mass spectra recorded. Comparison of the retention time shifts of these with the difference between those of the hydrogenated pheromone and the above model compound, indicated the acetoxy group in the pheromone was at the 5-position from the chain end. However, the EI mass spectrum of the hydrogenated pheromone suggested it was at the 8-position. 10-Acetoxy-heptadecan-2-one was synthesised, but the mass spectra and GC retention times of this indicated that the hydrogenated pheromone was indeed the 13-acetoxy-heptadecan-2-one, i.e. with the acetoxy group at the 5-position from the chain end.

Comparison of the CI mass spectra of the pheromone and hydrogenated pheromone showed that several ions in the former were due to the presence of the double bond. Thus, the 13-acetoxy-8-heptadecen-2-one structure was proposed and synthesised. The synthetic compound had GC retention times identical with those of the pheromone, on both columns, and the same EI and CI mass spectra. Furthermore, hydrogenation of this compound gave a compound with retention times and mass spectra identical with those of the hydrogenated pheromone.

The synthetic route was designed to give predominantly (>95%) the Z isomer. GC-MS analysis of the product showed a small peak (4%) following the major peak with identical mass spectra, and this was suspected to be the E isomer. This was supported by the observation that, when the hydrogenation was followed by GC analysis, this minor peak increased in size as the reaction progressed, presumably due to isomerisation on the catalytic surface prior to hydrogenation. Continued hydrogenation resulted in a single GC peak corresponding to the saturated compound.

EXAMPLE 2

Synthetic Routes

One of the compounds of the invention, 13-acetoxy-8-heptadecen-2-one, was synthesised by the following procedures. The route used to synthesise the racemic material for structure confirmation is shown in Scheme 1. All steps proceeded cleanly in good yield, with the exception of the Wittig coupling with 5-hydroxypentanal which, initially, gave a yield of 10%.

cylidene)-1,2-cyclohexanediaminecobalt(II)). The chiral epoxy-aldehydes are coupled with the phosphonium salt used in Scheme 1, and the epoxide is opened stereospecifically with propylmagnesium bromide in the presence of cuprous chloride.

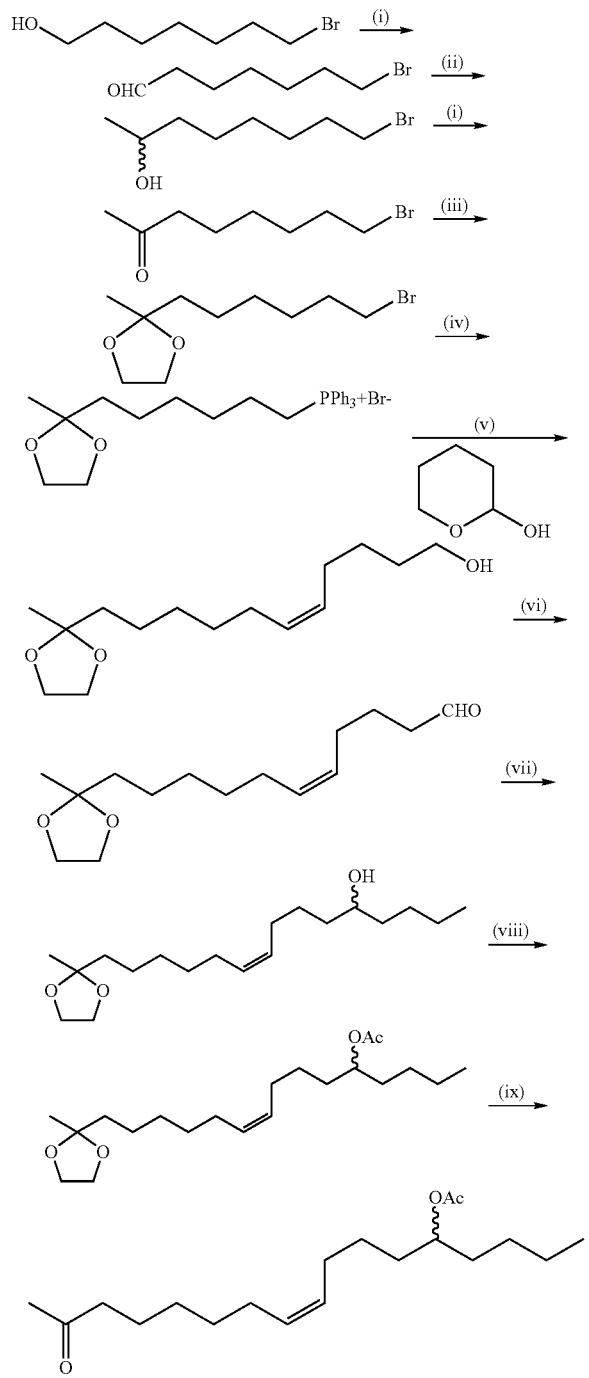

(i) PCC/CH$_2$Cl$_2$; (ii) CH$_3$MgI/ether; (iii) ethylene glycol/toluene/pTSA; (iv) PPh$_3$/CH$_3$CN; (v) 5-hydroxypentanal/NaHMDS/THF/-50° C.; (vi) PDC/CH$_2$Cl$_2$; (viii) BuMgBr/ether; (viii) Ac$_2$O/pyr; (ix) acetone/pTSA.

A synthesis of the R and S enantiomers is as shown in Scheme 2. Terminal epoxides are resolved into the enantiomers by selective hydrolysis in the presence of Jacobson's catalyst ((R,R)— or (S,S)—N,N'-bis(3,5-di-tert-butylsali-

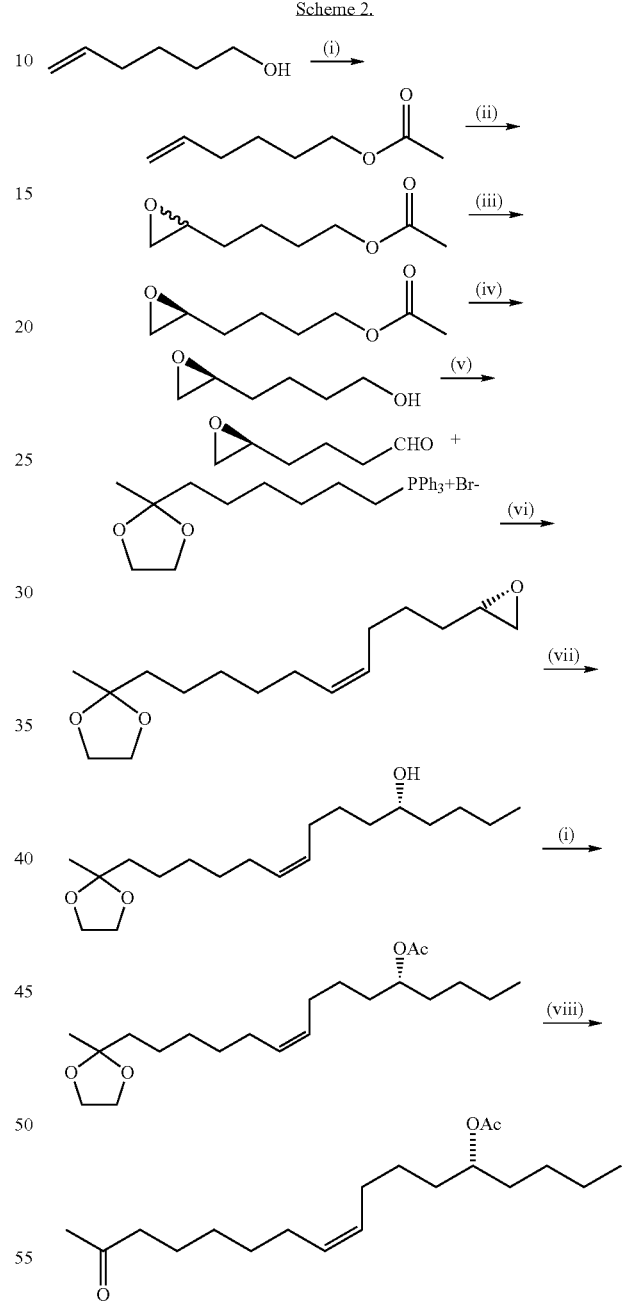

(i) Ac$_2$O/pyr; (ii) mCPBA/CH$_2$Cl$_2$; (iii) Jacobson's catalyst/THF/water; (iv) K$_2$CO$_3$/MeOH; (v) PCC/CH$_2$Cl$_2$; (vi) NaHMDS/THF; (vii) C$_3$H$_7$MgBr/CuI/ether; (viii) acetone/pTSA.

A preferred synthesis for racemic 13-acetoxy-8-heptadecen-2-one is as shown in Scheme 3. Racemic 13-acetoxy-8-heptadecen-2-one was synthesised on a 20 g scale in eight steps from commercially available 6-bromo-hexanoic acid. The overall yield was 63% of distilled material (175° C./0.04 mm Hg).

Scheme 3.

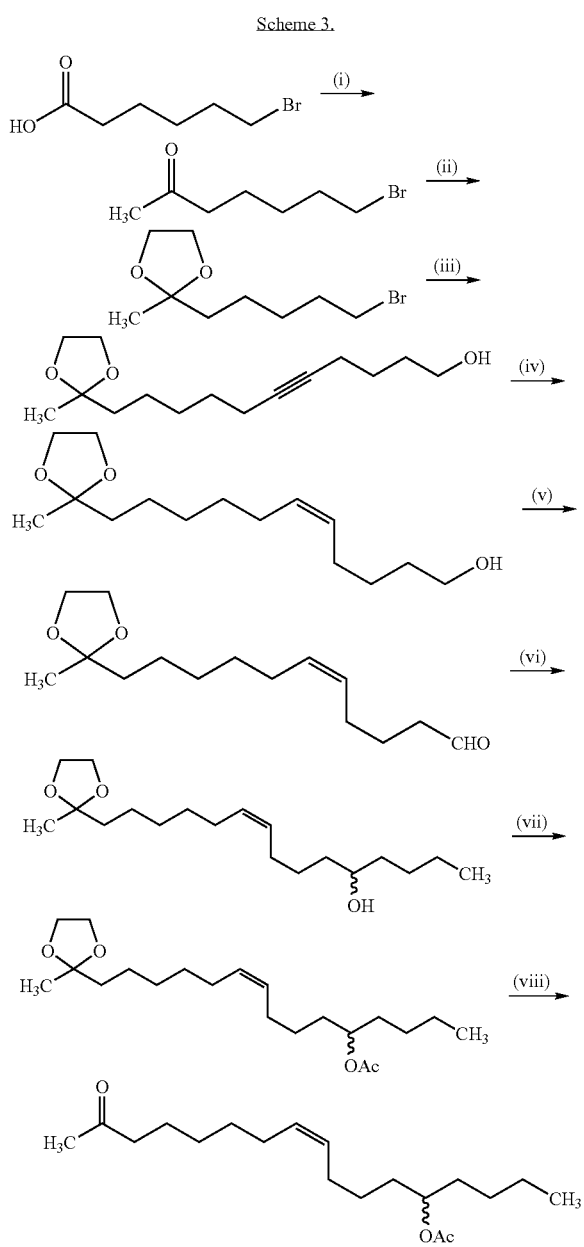

(i) MeLi/ether; (ii) ethanediol/benzene/pTSA; (iii) Li/liq NH₃/THF/ 5-hexyn-1-ol (81%); (iv) H₂/Lindlar catalyst/THF/petroleum spirit; (v) (COCl)₂/DMSO/CH₂Cl₂/Et₃N (85%); (vi) BuMgBr/ether; (vii) Ac₂O/pyridine; (viii) acetone/pTSM (91%).

EXAMPLE 3

Field Studies Using Racemic (Z)-13-acetoxy-8-heptadecen-2-one

A) Sticky delta traps baited with the synthetic lures impregnated with racemic (Z)-13-acetoxy-8-heptadecen-2-one were deployed in apple orchards. Large numbers of male apple leaf midges were caught in traps baited with the compound dispensed into the atmosphere from rubber septa. In an initial experiment in orchards at East Malling, Kent, UK, in 2004 comparing numbers of male midges caught in 5 replicate sticky delta traps, rubber septa impregnated with 100 versus 10 micrograms of racemic (Z)-13-acetoxy-8-heptadecen-2-one caught averages of 4037 and 1201 male midges between 7 May and 20 May 2004, compared to an average catch of 2 male midges in control traps that did not contain a lure.

B) Rubber septum lures impregnated with 10 versus 3 versus 1 microgram of racemic (Z)-13-acetoxy-8-heptadecen-2-one caught averages of 273, 97 and 12 male apple leaf midges respectively between 24 and 27 May 2004, compared to an average catch of 0.8 in the control traps with no lure, indicating that lures containing 1 microgram of (Z)-13-acetoxy-8-heptadecen-2-one can be effective for pest monitoring purposes.

C) Delta traps baited with lures containing 100 micrograms of racemic (Z)-13-acetoxy-8-heptadecen-2-one at distances of 10 m, 20 m, 30 m, 40 m and 50 m from an isolated apple orchard at East Malling, Kent, UK, infested with the midge, caught 563, 348, 148, 266 and 103 males respectively between 19 and 27 May 2004, indicating that the lures can attract significant numbers of males at distances of at least 50 m.

EXAMPLE 4

Identification of Natural Pheromone of Raspberry Cane Midge (*Resseliella thieobaldi* (Barnes))

Collection and Rearing of Virgin Midges:

Mature raspberry cane midge larvae were collected from two infested commercial raspberry plantations of the primocane varieties Autumn Bliss and Joan Squire at Beech Farm, West Peckham, Kent on 27 and 28 of July 2004. Sections of primocane with splits and characteristic patch lesions caused by the midge of up to 25 cm length were cut from the canes and stored in ventilated plastic boxes which contained a layer of moistened paper towel in the base. The boxes each contained about 20 cane sections and were kept on the laboratory bench. Many of the mature larvae exited the lesions underneath the epidermis seeking sites to pupate on the side, lid or in the base of the boxes or they pupated in situ. Over a period of 16 days, these mature larvae were collected and transferred individually to small transparent closed tubes (internal volume approximately 2 ml) (Autoanalyser cups with caps; Sarstedt, 68 Boston Road, Leicester LE4 1AW). A small piece of moist filter paper was included in each tube to prevent desiccation. The tubes were held in plastic trays in incubators at approximately 18° C. and 16L:8D. Adult midges started to emerge on 16 August. Each day, the newly emerged, virgin adults were collected, sexed and transferred to the entrainment apparatus.

Collection of Volatiles from Virgin Midges:

Pheromone was collected from virgin female midges by passing charcoal-purified air over the midges in a glass container (15 cm×5 cm) and trapping volatiles on Porapak Q (200 mg; 50/80 mesh; Supelco). Before use, the Porapak was Soxhlet extracted with chloroform for 8 hr, and the filters were washed well with dichloromethane immediately prior to collections. Trapped volatiles were eluted with dichloromethane (Pesticide grade; 3×0.5 ml) and the resulting solutions stored at 4° C. A low airflow rate of approximately 200 ml/min was used to minimise the desiccation stress to which the insects were subjected. Calling females stood motionless on the sides of the glass vessel with their ovipositors extended to expose the pheromone producing gland at the base from which the pheromone was emitted. Male midges flew around erratically. Raspberry cane midge adults have a short life of only 1-2 days, and dead midges were removed and fresh live females introduced each day. Porapak Q filters were changed approximately every week. Volatiles were collected from 987 female midges over a three week period. Volatiles were also collected from 633 males in an identical manner.

Analysis by Gas Chromatography (GC):

GC analyses were carried out on a capillary GC column (30 m×0.32 mm i.d.) coated with polar stationary phase (Wax 10; Supelco). Injection was splitless (220° C.) and detection by flame ionisation detection (FID; 250° C.). The oven temperature was programmed at 60° C. for 2 min then at 10° C./min to 250° C. Retention times are expressed as Retention Indices relative to the retention times of normal, saturated hydrocarbons.

GC analyses were also carried out on a column (25 mm×0.32 mm i.d.) coated with a chiral cyclodextrin stationary phase (Chirasil-Dex CB; Chrompack). Injection was splitless (220° C.) and detection by FID (250° C.). The oven temperature was programmed at 60° C. for 2 min then at 6° C./min to 250° C.

Analysis by Gas Chromatography linked to Mass Spectrometry (GC-MS):

GC-MS analyses were carried out with a Carlo Erba 5130 GC (Thermoelectron) linked directly to an ion trap detector (Finnigan ITD 700) operated in electron impact (EI) or chemical ionisation (CI) modes. The GC column (30 m×0.25 mm i.d.) was coated with polar Wax 10 (Supelco) and the oven temperature was programmed from 50° C. for 2 min, then at 6° C./min to 250° C.

GC-MS analyses were also carried out on a HP 6890 GC (Agilent) coupled directly to a HP 5973 MSD (Agilent) operated in EI mode. The GC column (30 m×0.25 mm i.d.) was coated with non-polar SPB1 (Supelco) and the oven temperature was programmed from 60° C. for 2 min, then at 6° C./min to 250° C.

Analysis by Gas Chromatography linked to Electroantennography (GC-EAG):

GC-EAG analyses were carried out with a BP 6890 GC (Agilent) fitted with capillary GC columns (30 mm×0.32 mm i.d.) coated with polar (Wax10; Supelco) and non-polar (SPB 1; Supelco) phases. Injection was splitless (220° C.) and detection was by FID (250°). The oven temperature was programmed from 50° C. for 2 min, then at 10° C./min to 250° C. The GC column effluent was split (1:1) between the FID and a silanised glass T-piece in the column oven. Nitrogen (500 ml/min) was blown continuously over the EAG preparation and every 17 sec this was diverted through the T-piece for 3 sec, blowing the contents over the EAG preparation, as described by Cork et al. (1991).

Following experience working with other midge species, the EAG preparation was set up by suspending the whole insect between glass electrodes containing electrolyte (0.1 M potassium chloride with 10% polyvinylpyrrolidone added to reduce evaporation). The ends of both antennae were inserted into the recording electrode and the body into the reference electrode. The electrodes were inserted into silver/silver chloride electrodes held in micromanipulators on the portable EAG device developed by Syntech (INR-02; Syntech, Hilversum, The Netherlands).

Results:

GC-MS Analyses:

Analyses of collections of volatiles from male and female midges showed four components in collections from females that were not present in collections from the males. These were a major component and three earlier-eluting minor components each present at approximately 30% of the major component. Retention Indices for these compounds relative to the retention times of normal hydrocarbons are shown in Table 1.

TABLE 1

GC retention data for female-specific components in GC-MS analyses

| Retention Index | | |
|---|---|---|
| Wax10 | SPB1 | Identification |
| 1600 | 1275 | 2-undecanone |
| 1665 | 1422 | 2-acetoxyundecane |
| 1722 | 1290 | 2-undecanol |
| 2091 | 1549 | 2-acetoxy-5-undecanone |

The three earlier-eluting minor components were identified as 2-undecanone, 2-acetoxyundecane and 2-undecanol from the spectral libraries and subsequent comparison of retention times and mass spectra with authentic standards. 2-undecanone and 2-undecanol are commercially available and 2-acetoxyundecane was synthesised by acetylation of 2-undecanol (Example 5).

Further examination of the chromatograms showed the corresponding 9-carbon compounds, 2-nonanone, 2-acetoxynonane and 2-nonanol, to be present at 1-2% of the major component in the collections from females but not in collections from males. Comparison of peak areas with those of standard acetates indicated that the major component was present at approximately 1.5 µg in a collection from a total of 200 females over a one week period. This is thirty times the amount of pheromone obtained from females of the apple leaf curling midge, Dasineura mal, under similar conditions.

GC-EAG Analyses:

In GC-EAG analyses of the collections of volatiles from female midges, an EAG response was always observed to the major female-specific component.

FIG. 1 of the accompanying drawings shows an example GC-EAG analysis of volatiles from female midges with male midge EAG preparation and polar GC column (GC lower trace, EAG upper trace). Major female-specific component is at 14.24 min; 2-undecanone at 9.07 min, 2-acetoxyundecane at 9.77 min and 2-undecanol at 10.45 min. EAG signals at 13.2 min and 14.9 min are probably interference spikes.

In the example shown in FIG. 1, there were also probably responses to the 2-acetoxyundecane and 2-undecanol, in addition to the major female-specific component.

Chemical Structure of the Major Pheromone Component:

The difference in retention data for the major female-specific component on the polar and non-polar GC columns (Table 1) indicated that this was much more polar than any of the minor components and probably had the deoxygenated functionality characteristic of several of the midge pheromones identified to date. The difference in retention indices on polar and non-polar columns for this component, 542, was midway between that for that of the diacetate structure (e.g. 493 for 2,12-diacetoxytridecane in the pea midge pheromone) and the unsaturated acetoxyketone found in the apple midge pheromone (657).

Figure 2A:
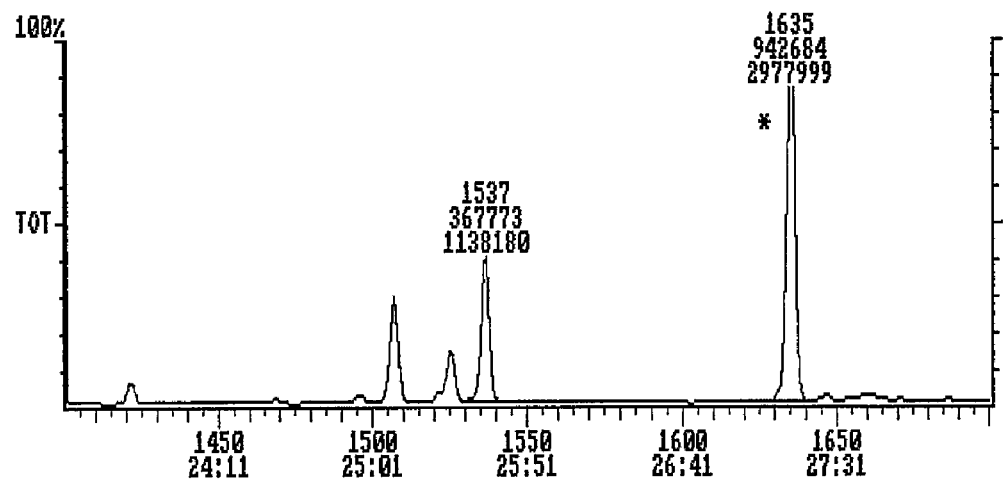
Figure 2B:
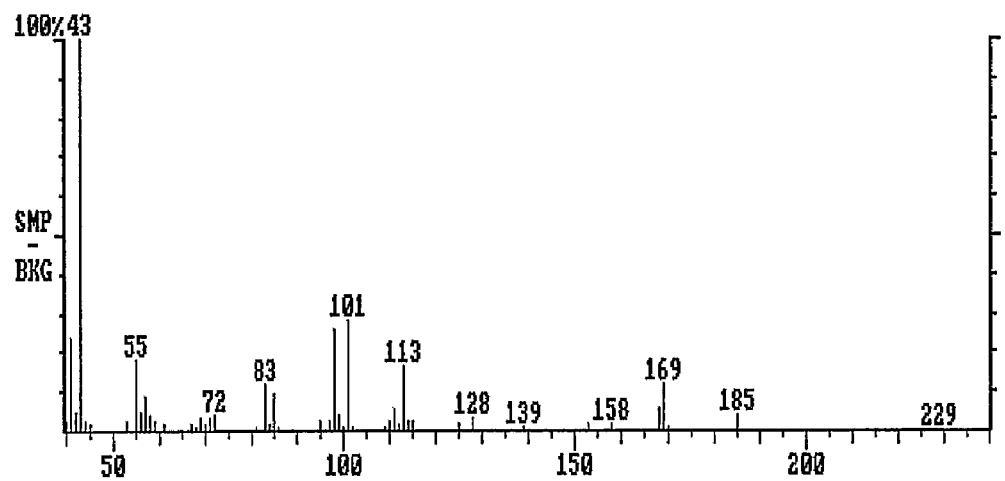
Figure 2C:
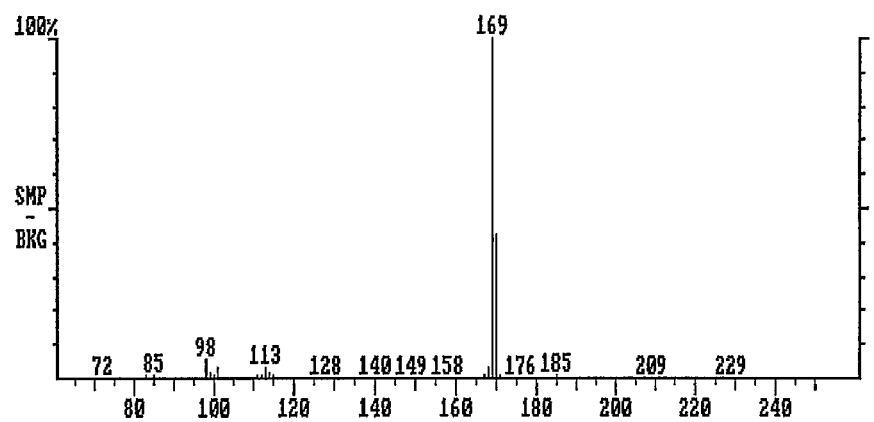

FIGS. 2a-c show GC-MS analyses of volatiles from female midges. FIG. 2a shows the Total Ion Trace (component at scan 1635); FIG. 2b shows the EI mass spectrum; FIG. 2c shows the CI (isobutane) mass spectrum The EI (FIG. 2b) and CI (FIG. 2c) mass spectra did not show a clear molecular ion, although the highest ion at m/z 229 suggested a molecular weight of 228 corresponding to a 11-carbon, saturated acetoxyketone. The ion at m/z 169 could then be due to the loss of acetic acid from an acetate, as further evidenced by the small ion at m/z 61. Hydrolysis of this component with potassium carbonate in methanol gave a product with longer GC retention time (R12117) giving a very broad peak.

Further analysis of the EI mass spectrum indicated the major component to be 2-acetoxy-5-undecanone, the structure of which could explain all the main ions in the mass spectrum.

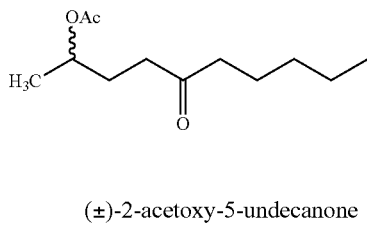

(±)-2-acetoxy-5-undecanone

Figure 3:
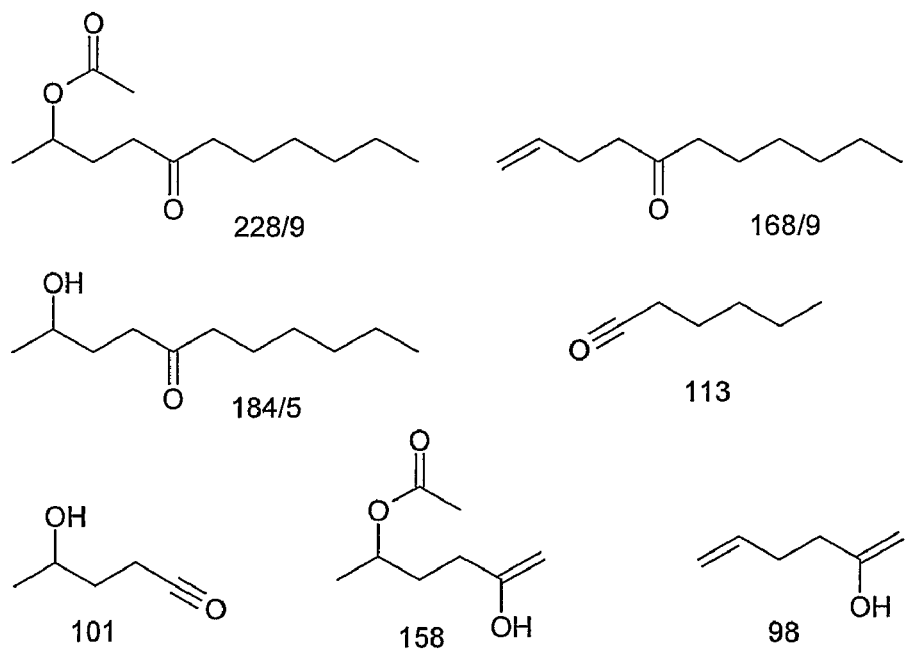

The proposed fragments in the EI mass spectrum of 2-acetoxy-5-undecanone are identified in FIG. 3. Hydrolysis of this compound would give the corresponding keto-alcohol, which could exist in cyclic on acyclic forms, and might be expected to give a broad peak on GC analysis.

Synthetic (±)-2-acetoxy-5-undecanone (Example 5) was found to have identical GC retention times and mass spectra to those of the natural female-specific component.

Chirality of Pheromone Components:

The enantiomers of the chiral pheromone components could be separated in analyses on the chiral Cyclodextrin GC column. Separations of the enantiomers of 2-acetoxyundecane and 2-acetoxy-5-undecanone were very good, but the enantiomers of 2-undecanol were only poorly separated.

Figure 4:
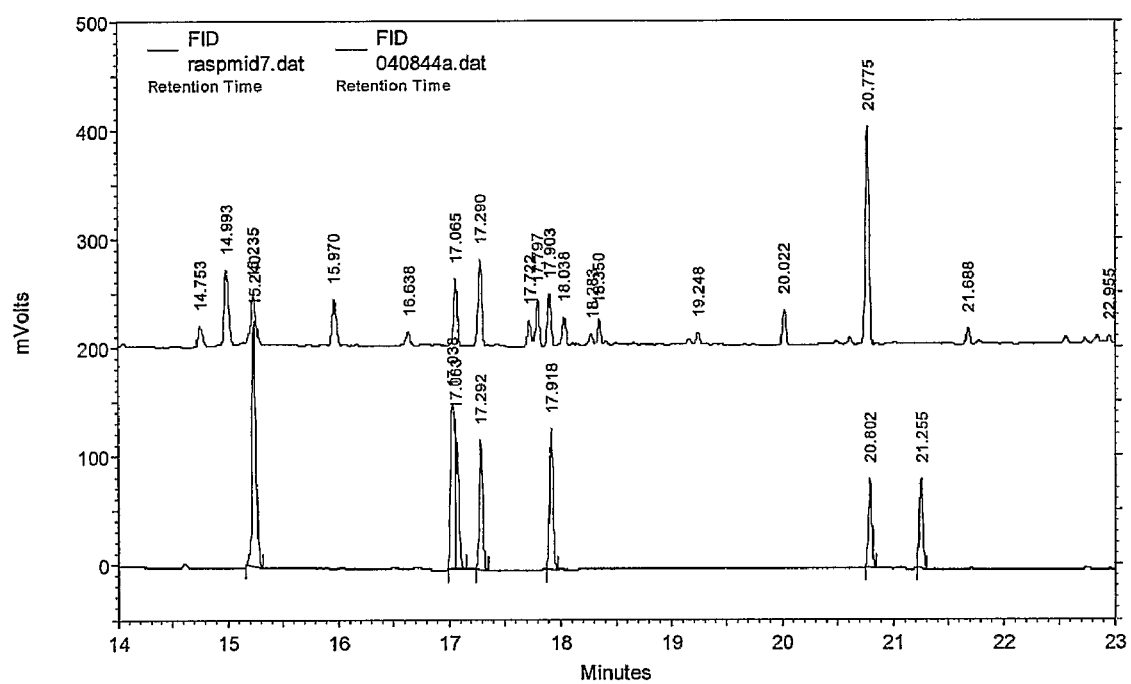

FIG. 4 shows the GC analyses on the chiral cyclodextrin column of synthetic standards (lower spectrum) and volatiles from female *R. theobaldi* (upper spectrum). The peaks are: 2-undecanone at 15.24 min; 2-undecanol at 17.04 and 17.06 min; 2-acetoxyundecane at 17.29 and 17.92 min; 2-acetoxy-5-undecanone at 20.80 and 21.26 min.

In analyses of the collections of volatiles from female midges, only a peak at the retention time of the first eluting enantiomer of the major pheromone component was present, and the later-eluting enantiomer could not be detected (<0.01%). The first-eluting enantiomer of 2-acetoxyundecane was present, but several impurity peaks made it impossible to be absolutely certain whether the other enantiomer was present or not. Enantiomers of 2-undecanol were poorly separated, but only the first-eluting enantiomer seemed to be present in the natural pheromone collections (FIG. 4).

Assuming the order of elution of the enantiomers on the Cyclodextrin column is the same as that reported for 2-acetoxytridecane (Choi et al., 2004), these results would suggest that the S enantiomers of the chiral pheromone components are produced by the female midges.

EXAMPLE 5

Synthetic Routes 2-acetoxy-5-undecanone

One of the compounds of the invention, 2-acetoxy-5-undecanone, was synthesised by the following procedures. The route used to synthesise the racemic material for structure confirmation is shown in Scheme 4. The product may be purified by flash chromatography and distillation (bp 130° C./0.02 mm).

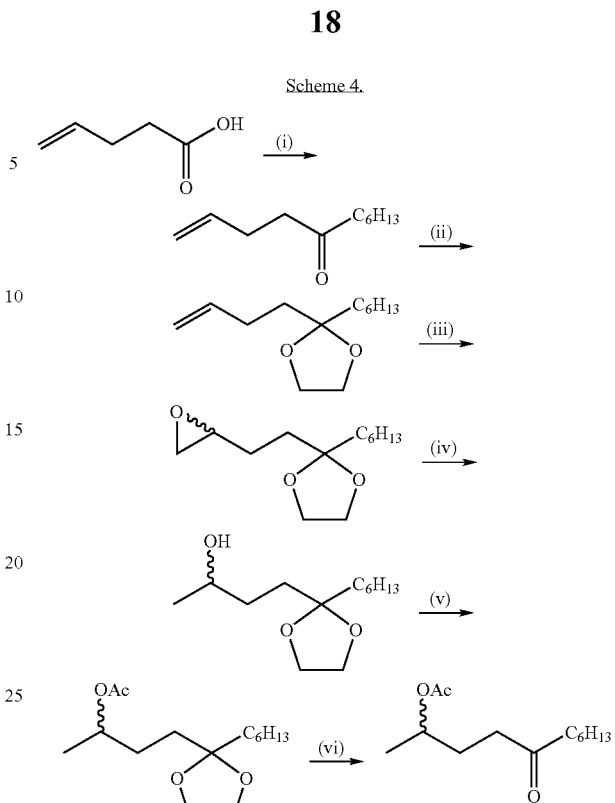

Synthesis of (±)-2-acetoxy-5-undecanone; reagents (i) hexyl lithium/ether; (ii) ethane diol/pTSA/benzene; (iii) 3-chloroperbenzoic acid/$CH_2Cl_2$; (iv) lithium aluminium hydride/ether; (v) acetic anhydride/pyridine; (vi) acetone/pTSA.

The separate enantiomers of 2-acetoxy-5-undecanone can be synthesised in a stereospecific manner by hydrolytic kinetic resolution of the epoxide intermediate from the synthesis of the racemic compound, as illustrated in Scheme 5.

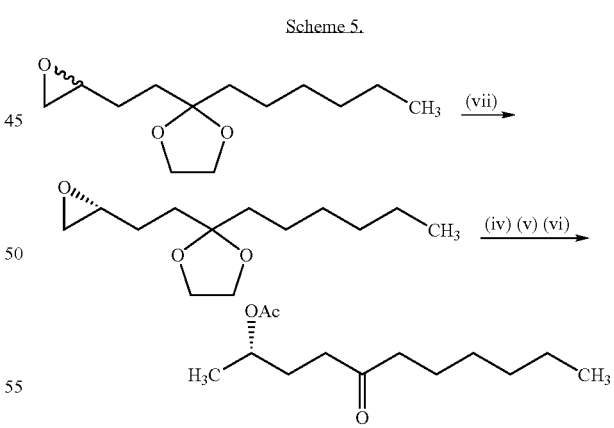

Synthesis of enantiomers of 2-acetoxy-5-undecanone (S enantiomer shown); reagents (vii) (R,R)-N,N'-bis(3,5-di-tert-butylsalicylidene)-1,2-cyclohexane-diaminocobalt (Jacobsen's reagent), acetic acid, THF, water; chromatography; (iv) lithium aluminium hydride/ether; (v) acetic anhydride/pyridine; (vi) acetone/pTSA (cf. Figure 2).

(±)-2-Acetoxyundecane

Acetylation of 2-undecanol with acetic anhydride in pyridine gave 2-acetoxyundecane (96%; bp 90° C./0.04 mm).

EXAMPLE 6

Field Studies Using Racemic 2-acetoxy-5-undecanone

A) Sticky traps baited with a rubber septum or polythene vial lure containing 100 microgrammes of racemic 2-acetoxy-5-undecanone were deployed in ten raspberry plantations at Belks farm, Otham, Kent, Beech Farm, West Peckham Kent and East Malling Research between 11 May and 31 May 2005. An average of 153 male raspberry cane midges were caught, per trap, compared to an average of 1 in similar traps not baited with a lure. This experiment established that racemic 2-acetoxy-5-undecanone is highly attractive to raspberry cane midge males.

B) A replicated field experiment was conducted in May and June 2005 in commercial raspberry plantations in Kent, UK to test the attractiveness of the major component of the raspberry cane midge sex pheromone, 2-acetoxy-5-undecanone, alone or in admixture with the three C11 compounds which were candidate minor components of the pheromone: 2-undecanol, 2-undecanone and 2-undecyl acetate. Sticky traps baited with a rubber septa or polythene vial lure containing 100 micrograms of racemic 2-acetoxy-5-undecanone alone or in admixture with 30 micrograms of racemic 2-undecanol, 30 micrograms of undecanone and 30 micrograms of racemic 2-undecyl acetate were deployed in ten raspberry plantations, 4 at Belks farm, Otham, Kent, 4 at Beech Farm, West Peckham Kent and 2 at East Malling Research, Kent between 11 May and 7 Jun. 2005 in a randomised complete block experimental design with the 10 different plantations as blocks.

The baited traps caught an average of 201 male raspberry cane midges per trap compared to an average of 1 in similar traps not baited with a lure. Analysis of variance of the total counts from each, after $\log_{10}$ (n+1) transformation to stabilise variances, followed by pairwise comparisons of means using the least significant difference (P=0.01), showed that there were no statistically significant differences between the catches in traps baited with lures containing the racemic 2-acetoxy-5-undecanone ('Major') alone or those containing a blend of racemic 2-acetoxy-5-undecanone with racemic 2-undecanol, undecanone and racemic 2-undecyl acetate ('Blend').

This experiment established that racemic 2-acetoxy-5-undecanone is highly attractive to raspberry cane midge males alone and the other three components are not essential and do not significantly (P=0.01) increase attractiveness at the lure loadings tested.

Table 2 shows mean total numbers of raspberry cane midge males caught in sticky traps baited with rubber septa or polythene vial lures containing racemic 2-acetoxy-5-undecanone alone (Major), or with a blend of 2-acetoxy-5-undecanone with racemic 2-undecanol, undecanone and racemic 2-undecyl acetate ('Blend').

TABLE 2

| Treatment | | Mean total number males captured per trap (n) | |
|---|---|---|---|
| Dispenser | Component(s) | n | $\log_{10}(n+1)$ |
| Septa | Major | 218 | 1.969 |
| Vial | Major | 230 | 2.042 |
| Septa | Blend | 333 | 2.269 |
| Vial | Blend | 222 | 2.058 |

TABLE 2-continued

| Treatment | | Mean total number males captured per trap (n) | |
|---|---|---|---|
| Dispenser | Component(s) | n | $\log_{10}(n+1)$ |
| No lure | None | 1 | 0.230 |
| Least significant difference (P = 0.01) | | | 0.3570 |

EXAMPLE 7

Rate of Release of Raspberry Cane Midge Pheromone Components from Lures

Measurements were made of the rates of release of the components from lures maintained in a laboratory wind tunnel at 27° C. and 8 km/hr wind speed. Volatiles were collected onto Porapak Q under same conditions for approximately 2 hours and the collections were analysed by Gas Chromatography with a flame ionisation detector using a polar column.

Table 3 shows mean release rates of pheromone components at increasing interval from two replicate rubber septa and two replicate polythene vials in a laboratory wind tunnel at 27° C. and 8 km/hr wind speed. Release rates (ng/hr) and their ratios to the major component are shown.

The results show that the lures were still releasing well after 26 days at 27° C., indicating that they should perform well in the field where average temperatures and wind speeds were considerably lower during the experiment. The septa released the components rapidly at first with the rate slowly reducing to less than 50% after 26 days. However, the ratios remained remarkably steady.

TABLE 3

| Interval (days) | Dispenser | 2-undecanone | 2-undecyl acetate | 2-undecanol | 2-acetoxy-5-undecanone |
|---|---|---|---|---|---|
| | | Mean release rate (ng/hr) | | | |
| 3 | Septa | 21.6 | 30.8 | 20.2 | 81.8 |
| 3 | Vial | 41.2 | 23.8 | 19.5 | 37.1 |
| 5 | Vial | 39.4 | 20.6 | 21.1 | 47.0 |
| 11 | Septa | 14.3 | 14.5 | 27.4 | 33.8 |
| 11 | Vial | 39.6 | 31.7 | 29.4 | 81.8 |
| 26 | Septa | 9.9 | 8.9 | 7.4 | 29.5 |
| 25 | Vial | 21.6 | 21.8 | 17.4 | 69.8 |
| | | Mean ratio | | | |
| 3 | Septa | 26 | 38 | 25 | 100 |
| 3 | Vial | 111 | 64 | 52 | 100 |
| 5 | Vial | 84 | 44 | 45 | 100 |
| 11 | Septa | 42 | 43 | 81 | 100 |
| 11 | Vial | 48 | 39 | 36 | 100 |
| 26 | Septa | 34 | 30 | 25 | 100 |
| 25 | Vial | 31 | 31 | 25 | 100 |

The invention claimed is:

1. A method to disrupt the mating patterns of, or to detect the presence of, a midge, said method comprising exposing a midge to an effective amount of a pheromone substance, wherein the pheromone substance is a straight-chain $C_{9-19}$ oxoalkyl or oxoalkenyl molecule substituted with a $C_{1-6}$ alkanoyloxy group, wherein the alkanoyloxy group or the oxo group is located at the 2-position.

2. A method according to claim 1, wherein the pheromone substance is present on a carrier which is a solvent or wicking material.

3. A method according to claim 1, wherein the oxoalkyl or oxoalkenyl molecule has between 11 and 17 carbons, inclusive, in the alkyl or alkenyl chain.

4. A method according to claim 1, wherein the $C_{1-6}$ alkanoyloxy group is linked to a methylene group.

5. A method according to claim 1, wherein the pheromone substance consists of the oxoalkyl or oxoalkenyl backbone possessing only the alkanoyloxy and oxo substituents.

6. A method according to claim 1, wherein the $C_{1-6}$ alkanoyloxy group is an acetoxy group.

7. A method according to claim 1, wherein the oxoalkyl or oxoalkenyl molecule has 9, 11, 13, 15, 17 or 19 carbon atoms.

8. A method according to claim 1, wherein the alkanoyloxy group is located at the 2-position and the oxo group is located at a position between 5- and 9-, inclusive.

9. A method according to claim 1, wherein the pheromone substance is a racemic mixture of two or more enantiomers.

10. A method according to claim 1, wherein the pheromone substance is singly unsaturated.

11. A method according to claim 1, wherein the pheromone is a heptadecene compound.

12. A method according to claim 10, wherein the double bond is located at a position between carbon atoms 4 and 13.

13. A method according to claim 12, wherein the double bond is located at position 8.

14. A method according to claim 10, wherein the oxo group is located proximal to the double bond and the alkanoyloxy group is located distal to the double bond.

15. A method according to claim 1, wherein the oxoalkenyl molecule has a single double bond, and wherein the configuration of the double bond is Z.

16. A method according to claim 1, wherein the pheromone substance is an acetoxyheptadecenone.

17. A method according to claim 1, wherein the pheromone substance is saturated.

18. A method according to claim 17, wherein the pheromone substance is an undecane.

19. A method according to claim 18, wherein the pheromone substance is a 2-alkanoyloxy, 5-oxo undecane.

20. A method according to claim 17, wherein the pheromone substance is an acetoxyundecanone.

21. A method according to claim 1, wherein the pheromone substance has the formula:

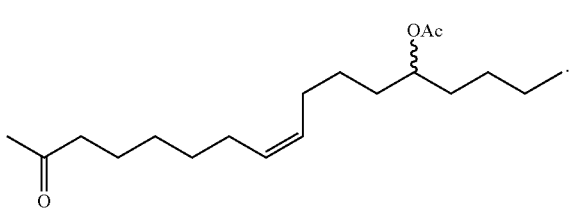

22. A method according to claim 1, wherein the pheromone substance has the formula:

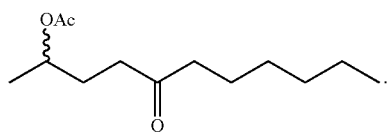

23. A method according to claim 1, wherein the pheromone substance comprises two compounds differing only with respect to the enantiomeric configuration of the alkanoyloxy group.

24. A method according to claim 1, wherein the midge is selected from the group consisting of grain, olive, raspberry, apple, blackcurrant, rhubarb, blackberry, plum, cherry, blueberry, cruciferae and rosaceae midges.

25. A method according to claim 24, wherein the midge is *Dasineura mali* and the pheromone substance has the formula:

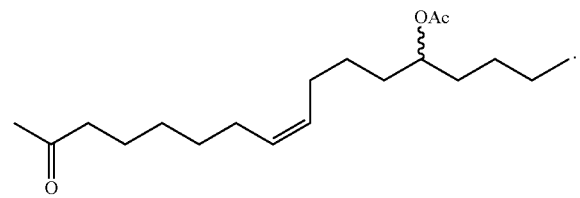

26. A method according to claim 24, wherein the midge is *Resseliella theobaldi* and the pheromone substance has the formula:

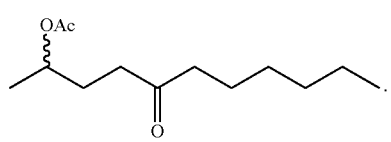

27. Pheromone dispensing apparatus useful to disrupt the mating patterns of, or to detect the presence of a midge, said apparatus equipped with a pheromone substance as described in claim 1.

28. Apparatus according to claim 27, adapted to dispense a gradient of pheromone, said gradient being detectable as a gradient by a midge.

29. Apparatus according to claim 27, which is a trap for the midge.

30. Apparatus according to claim 27, wherein the apparatus further comprises insecticidal means effective against the midge.

31. Apparatus according to claim 27, adapted to dispense said pheromone substance in amounts greater than are detectable as a gradient by the midge within a 100 meter radius of the apparatus for a selected duration.

32. A pheromone substance having the formula:

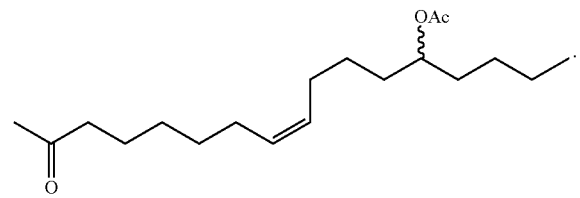

* * * * *